United States Patent [19]

Kempster et al.

[11] Patent Number: 5,444,367
[45] Date of Patent: Aug. 22, 1995

[54] METHOD AND APPARATUS FOR DETECTING PARTICLES IN A FLUID HAVING COILS ISOLATED FROM EXTERNAL VIBRATIONS

[75] Inventors: Robert W. Kempster, Ottawa; Douglas B. George, Kanata, both of Canada

[73] Assignee: Minister of National Defence, Ottawa, Canada

[21] Appl. No.: 143,661

[22] Filed: Nov. 1, 1993

Related U.S. Application Data

[63] Continuation-in-part of Ser. No. 866,885, Apr. 6, 1992, Pat. No. 5,315,243.

[51] Int. Cl.⁶ .................... G01N 27/74; G01R 33/12; G08B 17/10
[52] U.S. Cl. .................................. 324/204; 324/225; 340/631
[58] Field of Search ............... 324/204, 233, 236, 232, 324/225; 340/631; 73/61.42

[56] References Cited

U.S. PATENT DOCUMENTS

| | | |
|---|---|---|
| 2,215,605 | 9/1940 | De Lanty . |
| 3,231,815 | 1/1966 | Spencer . |
| 3,433,057 | 3/1969 | Halsey . |
| 3,665,298 | 5/1972 | Geiger .................... 324/41 |
| 3,676,773 | 7/1972 | Eckhardt ................ 324/41 |
| 3,748,576 | 7/1973 | Sigournay ............... 324/41 |
| 4,100,491 | 7/1978 | Newman, Jr. et al. .... 324/204 |
| 4,144,741 | 3/1979 | Nakamoto et al. ....... 73/19 |
| 4,176,545 | 12/1979 | Oddo ...................... 73/64 |
| 4,219,805 | 7/1980 | Magee et al. ............ 340/631 |
| 4,300,097 | 11/1981 | Turner .................... 324/329 |
| 4,563,644 | 1/1986 | Lenander et al. ........ 324/232 |
| 4,651,091 | 3/1987 | Chambers et al. ....... 324/204 |
| 4,651,092 | 3/1987 | Brunsch et al. ......... 324/204 |
| 4,692,698 | 9/1987 | Lewis ..................... 324/204 |
| 4,731,578 | 3/1988 | Tsapraxis ................ 324/204 |
| 4,766,373 | 8/1988 | Chambers et al. ....... 324/204 |
| 4,785,239 | 11/1988 | Brunsch et al. ......... 324/204 |
| 4,926,120 | 5/1990 | Veronesi et al. ......... 324/204 |
| 5,001,424 | 3/1991 | Kellett et al. ............ 324/204 |
| 5,041,856 | 8/1991 | Veronesi et al. ......... 324/236 |

FOREIGN PATENT DOCUMENTS

| | | |
|---|---|---|
| 1348881 | 3/1974 | United Kingdom . |
| 2101330 | 1/1983 | United Kingdom . |
| 2190503 | 11/1987 | United Kingdom . |
| 8504715 | 10/1985 | WIPO . |

*Primary Examiner*—Walter E. Snow
*Attorney, Agent, or Firm*—Dressler, Goldsmith, Shore & Milnamow, Ltd.

[57] ABSTRACT

A device to detect the presence of particles, principally metallic particles, in fluid lines. The fluid to be sampled flows through a former on which is wound a coil assembly comprising a sensor coil flanked upstream and downstream by two field coils. The former is constructed with a double wall and air gap such that pressure fluctuations in the fluid are not transmitted to the coil assembly to adversely affect the positions and readings of the coils. The field coils are driven by a high frequency signal derived from a crystal oscillator and the upstream and downstream sections are wound in opposite directions such that the magnetic field from each section is cancelled out in the plane of the sense coil. When a ferromagnetic or conductive particle passes through the winding structure, the coupling in the sense coil is disturbed as the particle first interacts with the field in the upstream section of the field coil and later with the field in the downstream section of the field coil as it passes through the Sensor Coil Assembly (SCA). A characteristic signature is generated in the sense coil which results from the vector summation of these transient imbalance signals with the steady-state signal from the opposed field coils. Analysis of the phase of this signature can be used to detect and distinguish between the presence of ferromagnetic and non-ferromagnetic conductive particles. Since ferromagnetic and non-ferromagnetic conductive particles interact with the field via permeability and eddy current effects respectively, the transient phase signature has a characteristic lag-lead or lead-lag sequence depending on the nature of the particle.

12 Claims, 14 Drawing Sheets

A cos wt f(t)cos wt

1 × 2

A'f(t) cos²wt

LPF

A''f(t)

DC BLOCK & GAIN

FIG.14a
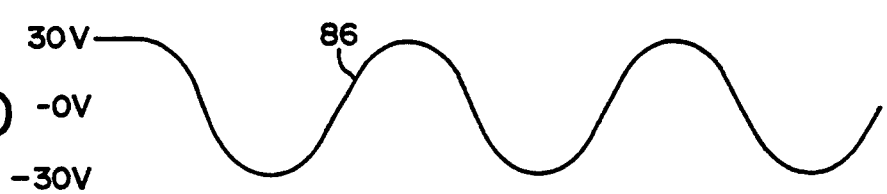
FIG.14b
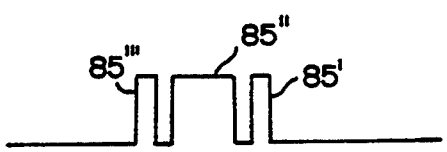
FIG.14c
FIG.15
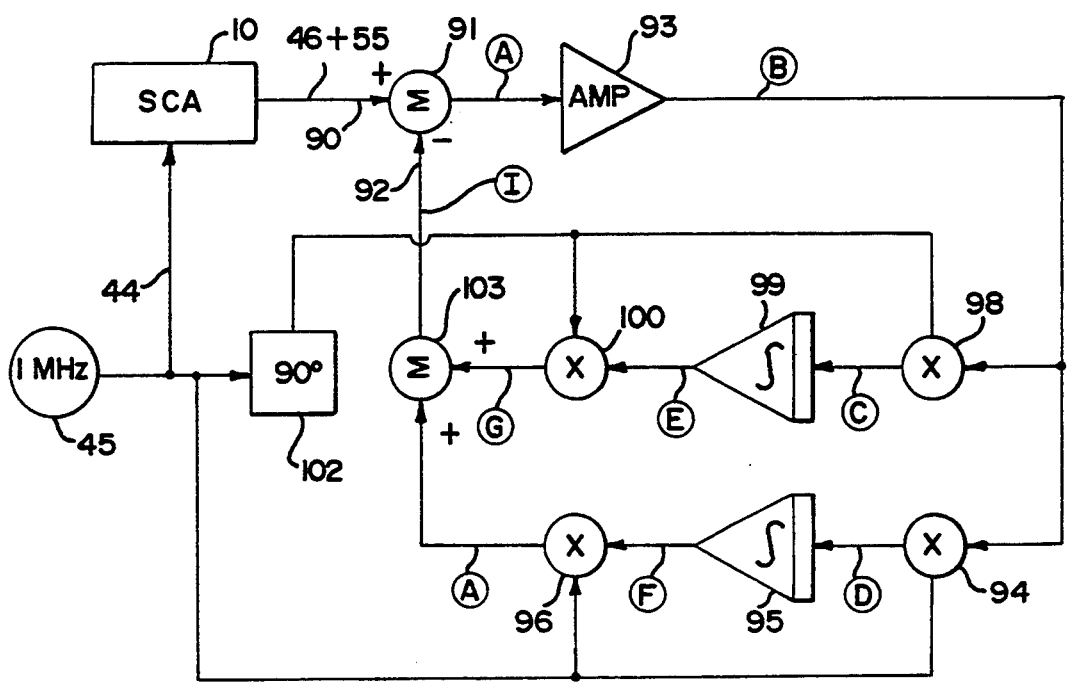

METHOD AND APPARATUS FOR DETECTING PARTICLES IN A FLUID HAVING COILS ISOLATED FROM EXTERNAL VIBRATIONS

RELATED APPLICATIONS

This is a continuation-in-part application of application Ser. No. 07/866,885 filed Apr. 6, 1992, now U.S. Pat. No. 5,315,243.

The present invention relates to a method and an apparatus for detecting the presence of particles in a fluid, particularly but not exclusively, the presence of metal particles in lubricating oil caused by wear in machinery.

BACKGROUND OF THE INVENTION

One technique for detecting on a real time basis the presence of particles in oil that has found wide acceptance is described in U.S. Pat. No. 4,651,091, inventors Chambers and Waggoner, issued Mar. 17, 1987.

However, the technique described in that patent cannot discriminate between ferromagnetic and non-ferromagnetic particles.

U.S. Pat. 5,001,424, inventors Kellett and Erickson, issued Mar. 19, 1991, also describes apparatus for detecting the presence of particles in oil but again no means for discriminating between ferromagnetic and non-ferromagnetic particles s suggested. Additionally, Kellett et al do not suggest a satisfactory technique for compensating for residual signals caused by imbalance of the opposing magnetic fields. In fact, the circuit proposed by Kellett et al would not operate satisfactorily without considerable modification to improve sensitivity and remove the effects of noise.

SUMMARY OF THE INVENTION

It is an object of the invention to provide an improved apparatus for detecting the presence of particles in a fluid.

The apparatus has a sense coil assembly mounted on a tubular former through which the fluid flows. In accordance with one aspect of the invention the former is constructed with a double wall and air gap such that pressure fluctuations in the fluid are not passed through the former to the sense coil assembly to cause movement of the coils and adversely affect readings.

In order to isolate the coil assembly from mechanical vibrations or impacts to the housing surrounding the apparatus, the coils may be carried on a coil support sleeve the bore of which receives the outer tube and the outer surface of which engages an inner shield mounted on the housing in such a manner as to prevent movement of the housing being transmitted to the coils.

In another aspect, the field and sense coils are each arranged in a resonant circuit so as to increase the sensitivity of the device by as much as 600. This sensitivity can be further improved by arranging the drive circuit of the field coils as a pulse driven class C amplifier.

To remove the residual imbalance signal the instant invention proposes two different types of autobalance circuits, one using control loops controlling the amplitude of two quadrature signals and the other controlling the phase and amplitude of a single signal.

As an alternative to analog processing of the signature output, the invention proposes a matched filter digital approach.

BRIEF DESCRIPTION OF THE DRAWINGS

FIGS. 14a, b and c are waveform diagrams illustrating the operation of the circuit of FIG. 13;

FIG. 15 is a block diagram illustrating an improved autobalance circuit;

DETAILED DESCRIPTION OF A PREFERRED EMBODIMENT

Figure 1:
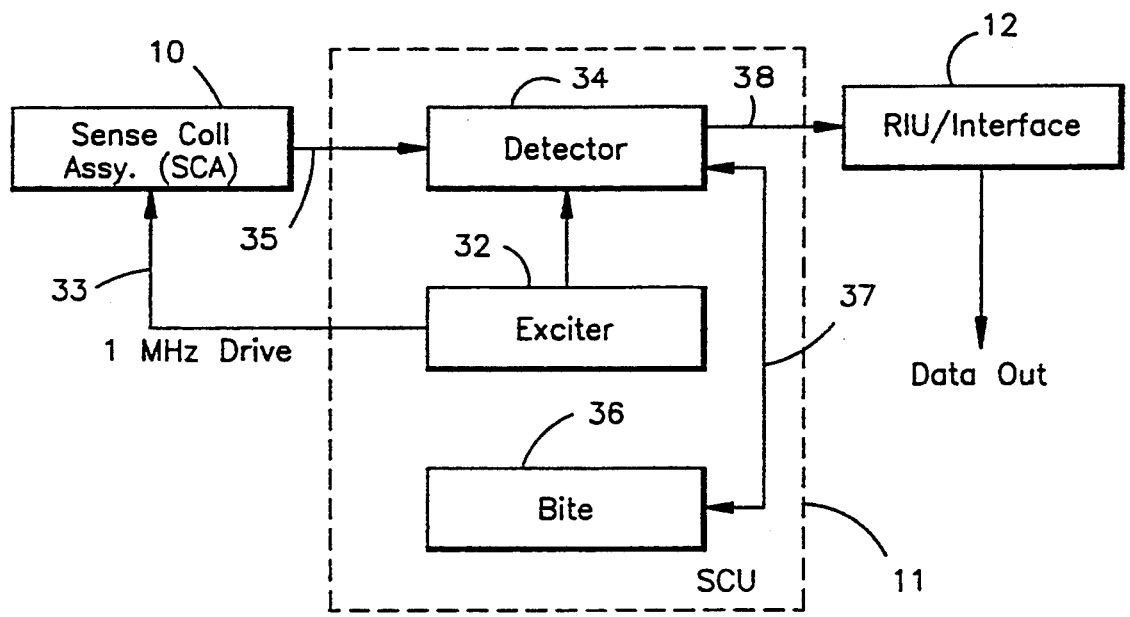
FIG. 1 is a functional block diagram of a particle detector according to the invention.
Figure 2:
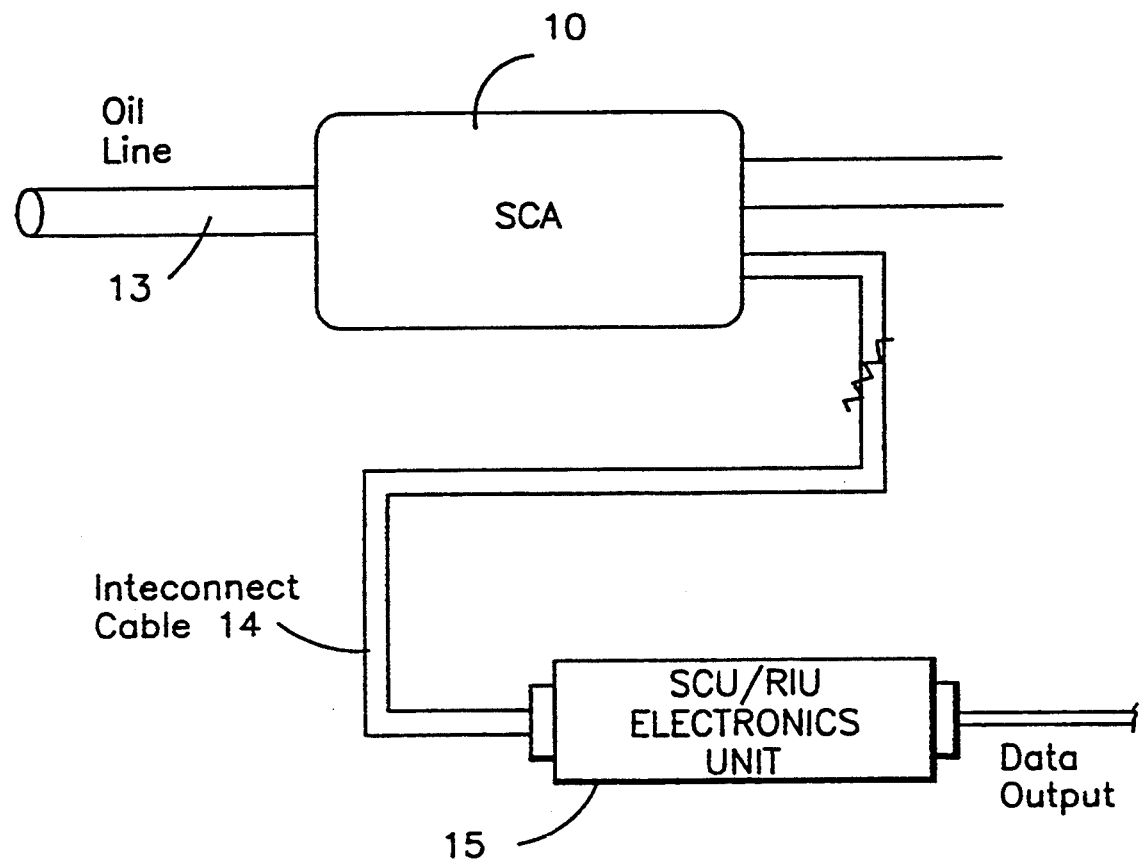
FIG. 2 illustrates the mechanical configuration of the particle detector of FIG. 1.

With reference to FIG. 1, the particle detector of the invention comprises a sense coil assembly (SCA) 10, a signal conditioning unit (SCU) 11 and a readout interface unit (RIU) 12. As shown in FIG. 2, the SCA 10 in use is mounted on an oil pipe 13 and is interconnected by means of a cable 14 to the SCU 11 and RIU 12 which are packaged together at a remote location in an electronics unit 15.

Figure 3:
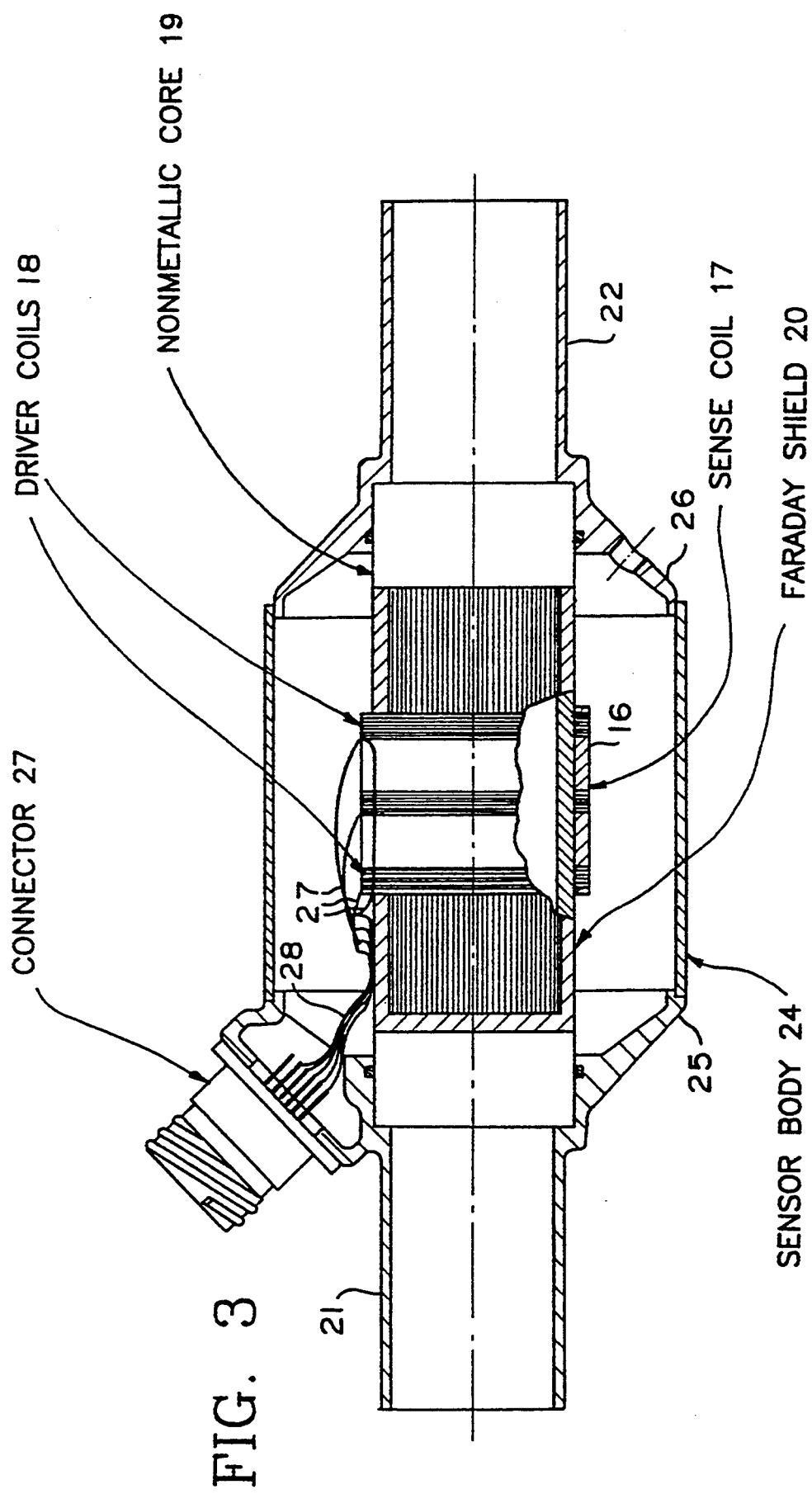
FIG. 3 is a longitudinal sectional view of a sensor coil assembly, which forms part of the particle detector, shown in situ.

Referring now to FIG. 3, the SCA 10 comprises a bobbin 16 on which are wound a copper sense coil 17 located equidistantly from upstream and downstream field or drive coils 18, the two field coils being wound in opposite senses from each other. The bobbin is carried on a non-metallic cylindrical core or former 19 which may be made of a high-temperature-resistant sintered plastic material such as TORLON. The bobbin may also be made of TORLON or ceramic, with a Faraday shield 20 sandwiched between the bobbin and the core 19. A layer of insulation may be applied over the Faraday shield.

The non-metallic core 19 is coupled at each end to a pipe section 21 and 22 which is adapted to be connected into the oil line 13 (FIG. 2). A cylindrical sensor body 24 extends between widened diameter portions 25 and 26 of pipe sections 21 and 22 such that sensor body 24 is generally concentric with and surrounds core 19 in spaced relation thereto. Body 24 serves to provide physical protection for the coils and other components of the SCA and to provide shielding from external electromagnetic fields and typically is made from aluminum. Leads 27 from the coils are gathered together into a harness 28 which is adapted to be connected to the cable 14 via a connector 29.

Referring again to FIG. 1, the SCU 11 comprises three blocks, namely an exciter 32 connected to drive the SCA via a line 33, a signal detector 34 connected to an output 35 of SCA 10 and built-in test equipment (BITE) circuits 36 connected to detector 34 via line 37 for inserting and detecting a test signal to verify operation of the entire sensing system. An output 38 of detector 34 is connected to an input of RIU 12.

In operation, with clean (i.e. lacking metallic particles) oil flowing through oil line 13 and a 1 MHz drive signal being fed from exciter 32 to the field coils 18, there is essentially no output signal from the sense coil 17 since the field coils are wound in opposite directions thereby causing two magnetic fields generated in the plane of the sense coil by the field coils to be substantially balanced and cancelled out.

However, when a ferromagnetic particle present in the oil passes into the region of the upstream field coil, it increases the magnetic coupling between the upstream field coil and the sense coil and later, as it passes into the region of the downstream field coil, it increases the magnetic coupling between the downstream field coil and the sense coil. When a non-ferromagnetic conductive particle present in the oil passes into the region of the upstream field coil, it decreases the magnetic coupling between the upstream field coil and the sense coil and later, as it passes into the region of the downstream field coil, it decreases the magnetic coupling between the downstream field coil and the sense coil. These phenomena give rise to a varying signal derived from the sense coil which is detected and processed in detector 34 and the output of the detector is then used to give a readout via RIU 12 of data relating to the particle.

The sensing and processing of the sensed signal will be described in detail hereinbelow. Suffice it to say, for the time being, that the sense coil produces a characteristic output which signifies whether the particle is ferromagnetic or non-ferromagnetic and indicates the size of the particle.

Figure 4:
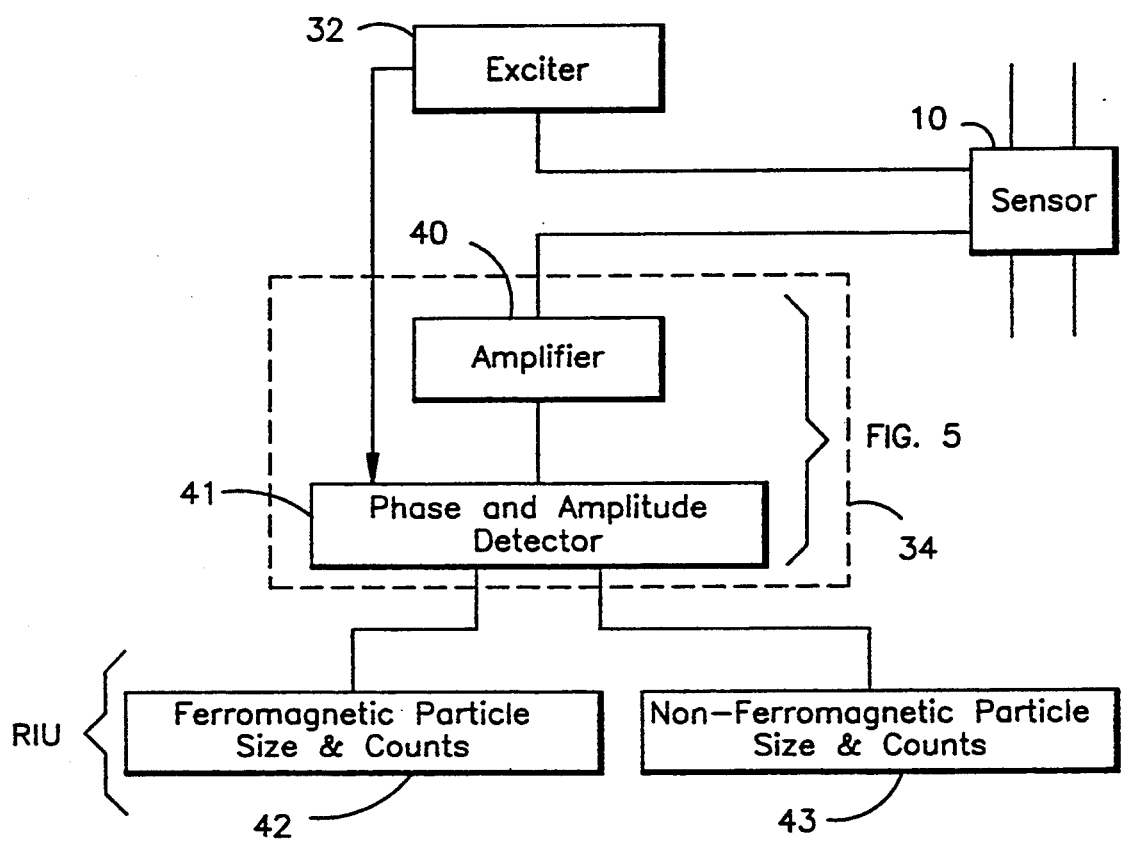
FIG. 4 is a more detailed block diagram of the detector illustrated in FIG. 1.

FIG. 4 is a slightly more detailed version of FIG. 1 and shows detector 34 as comprising an amplifier block 40 feeding a phase and amplitude detector 41. The RIU 12 of FIG. 1 is shown in FIG. 4 as two blocks 42 and 43 for counting and indicating size of ferromagnetic particles and non-ferromagnetic particles, respectively.

Figure 5:
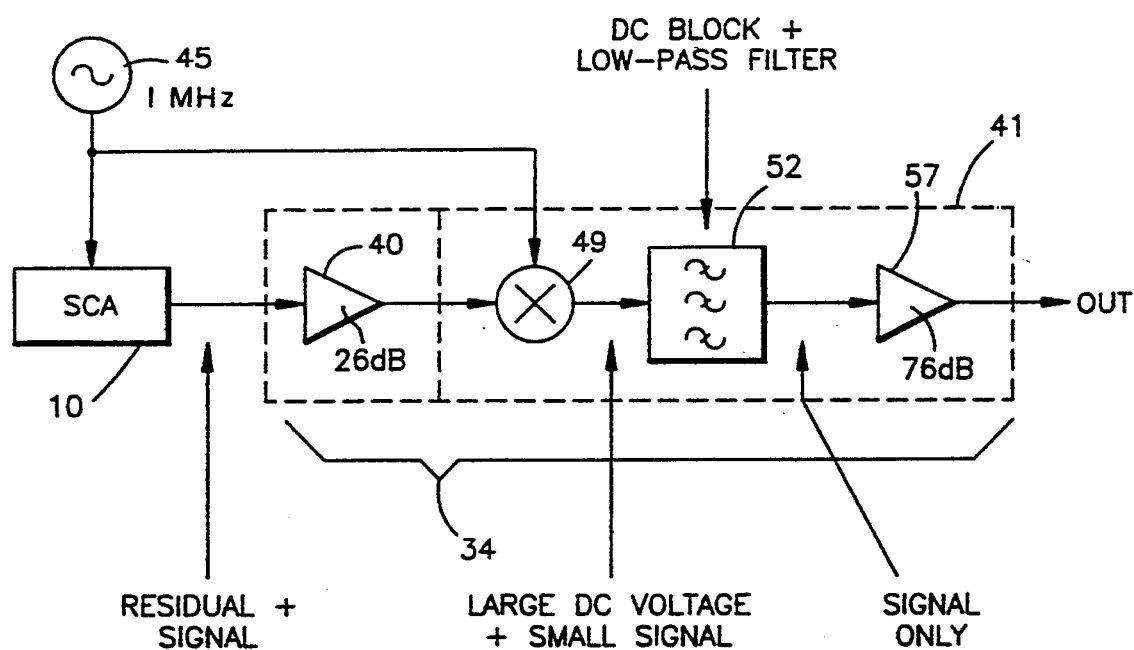
FIG. 5 is a block diagram illustrating in greater detail the components of FIG. 4.

Reference should now be made to FIG. 5 in conjunction with FIGS. 6 and 7 for a more detailed operation of the invention. A 30 volt 1 HHz drive signal 44 shown at FIG. 6(a) is applied to SCA 10 from the exciter 32, shown schematically in FIG. 5 as an oscillator 45 which, in fact, forms only part of the exciter. If a ferromagnetic particle is present in the oil flowing through the particle detector, a characteristic signal 46 shown in FIG. 6(b) is generated by the sense coil 17. It can be seen that signal 46 has the same frequency as the drive signal 44 and is initially in phase with drive signal 44, the amplitude steadily increasing and then decreasing in value as the particle moves between the upstream field coil 18 and the sense coil 17. As the particle moves between the sense coil 17 and the downstream field coil 18 again the amplitude rises from zero through the maximum and back to zero but now the signal 46 is 180° out of phase with respect to signal 44.

Figure 6A:
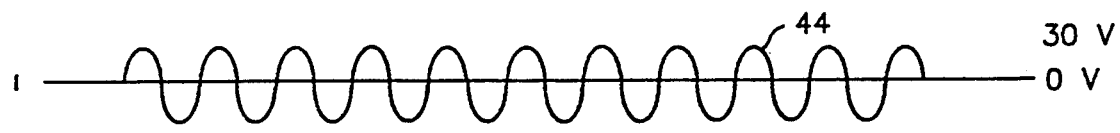
FIG. 6 is a diagram illustrating waveforms present at different points in FIG. 5.
Figure 6B:
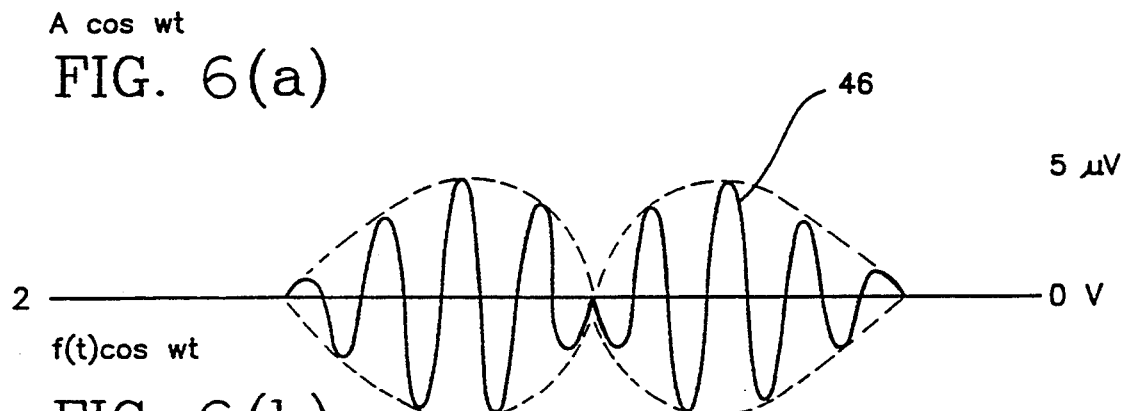
Figure 6C:
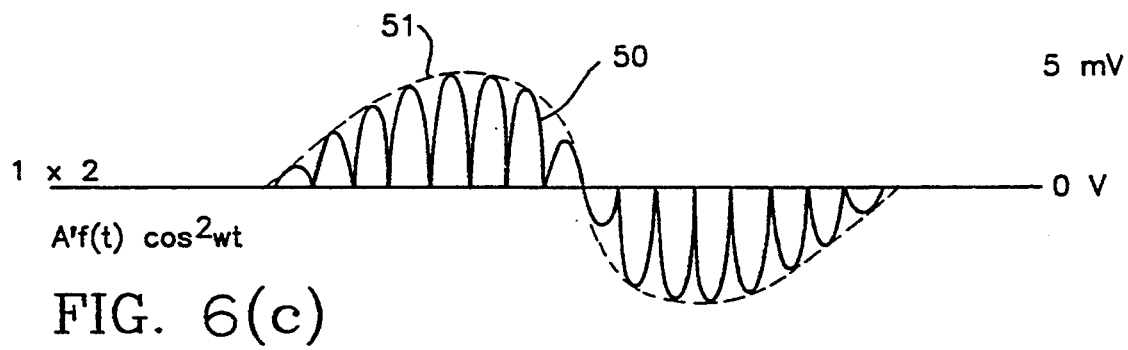

Signal 46 is fed from SCA 10 through amplifier 40 to a mixer 49 where it is mixed with a 1 MHz signal from the oscillator 45 to derive a signal 50 illustrated in FIG. 6(c). It can be seen that the envelope 51 of signal 50 is a sine wave which follows the positive envelope of signal 46 over the portion that signal 46 is in-phase with signal 44 and then follows the negative envelope of signal 46 over that portion of signal 46 where it is out of phase with signal 44.

Figure 6D:
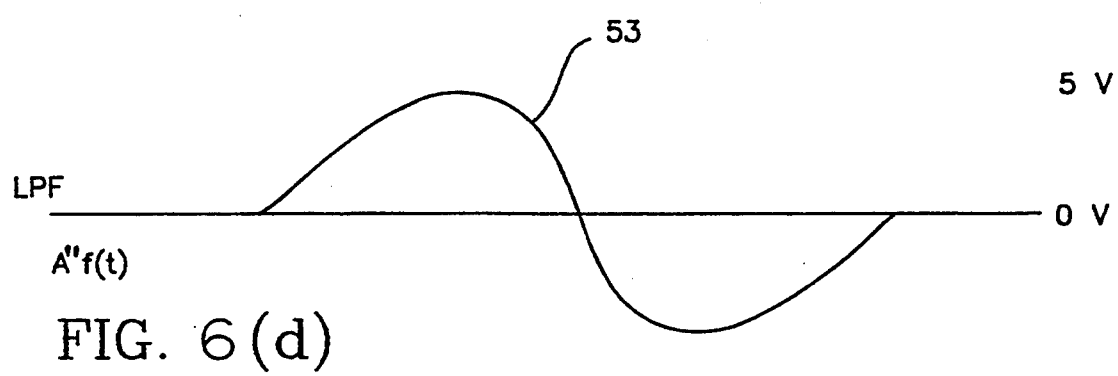
Figure 7A:
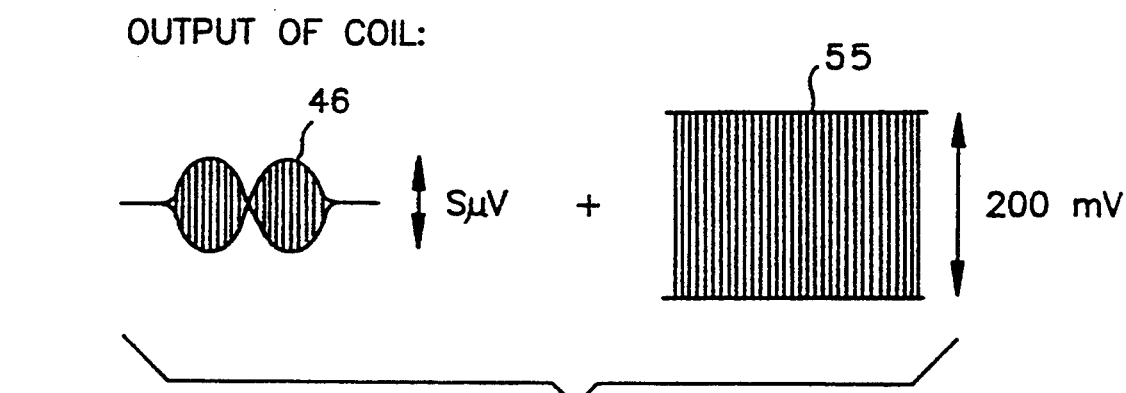
FIG. 7 is a diagram illustrating the function of a filter of FIG. 5.

Signal 50 is then passed through a low-pass filter 52 and amplified to obtain a signal 53, shown in FIG. 6(d), which is a sine wave following the envelope 51 of signal 50. Actually filter 52 is also constructed as a D.C. blocking filter as well as a low-pass filter for the following reason. If the field coils 18 are spaced exactly the same distance from the sense coil 17 and are wound accurately, in theory the two fields generated in the plane of the sense coil 17 should cancel. In practice, however, there is always some minor discrepancy and this gives rise to the derivation of a residual signal 55, which typically should be no larger than 200 mV, which is shown in FIG. 7(a) along with signal 46 which is the signal caused by the presence of a moving ferromagnetic particle.

Figure 7B:
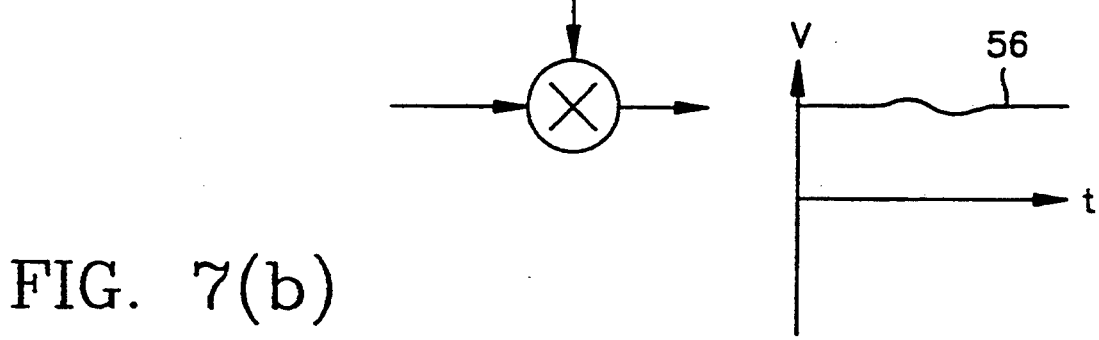
Figure 7C:

The output of mixer 49 is shown in FIG. 7(b) and this can be seen to be a D.C. component 56 on which is superimposed the signal 50 of FIG. 6(c). After passage through filter 52 the D.C. component 56 has been removed and the envelope 51 reproduced and after amplification by amplifier 57 the signal 53 shown in FIGS. 6(d) and 7(c) is obtained.

It is noted that the signal 53 indicates by its magnitude the size of the ferromagnetic particle detected. The duration of the signal simply indicates the speed at which the particle passed through the SCA 10, typically between 1 and 3 msecs. More importantly, the phase of signal 53 indicates whether the particle detected is ferromagnetic or non-ferromagnetic. This can be explained as follows. If a non-ferromagnetic particle, aluminum for example, had been detected, the sensed signal 46 would have comprised a first portion out of phase with drive signal 44 and a second portion in-phase with signal 44, i.e., exactly the opposite of signal 46 illustrated in FIG. 6(b). The reason for the difference is that non-ferromagnetic particles interact with the field via eddy currents rather than permeability in the case of ferromagnetic particles. The end result is that, in the case of a non-ferromagnetic particle, signal 53 would be the mirror image of signal 53 shown in FIG. 6(d) i.e., the first half of the signal would be negative and the second half positive.

Signal 53 can easily be processed by known techniques for example by means of threshold detectors to sample signal 53 and drive counters to indicate whether ferromagnetic or non-ferromagnetic and to indicate also the size of the particle. More particularly, if a negative threshold detector is tripped within a predetermined time after a positive threshold detector has been tripped, this indicates a positive signal half followed by a negative signal half as illustrated in FIG. 7(c), thereby signalling a ferromagnetic particle. If, on the other hand, the positive threshold detector is tripped after the negative threshold detector, this indicates a mirror image of the signal 53 shown in FIG. 7(c), thereby signalling a non-ferromagnetic particle. These functions as well as counting the actual number of particles sensed are generally referred to by blocks 42 and 43 in FIG. 4.

A potential problem arises from the presence of air or water bubbles in the oil which give rise to interaction with electric fields causing spurious signals or noise to be detected in the sense coil 17. The Faraday shield 20 is located between the coils and the fluid, effectively blocking electric fields and avoiding spurious signals resulting from the presence of air bubbles.

Figure 8:
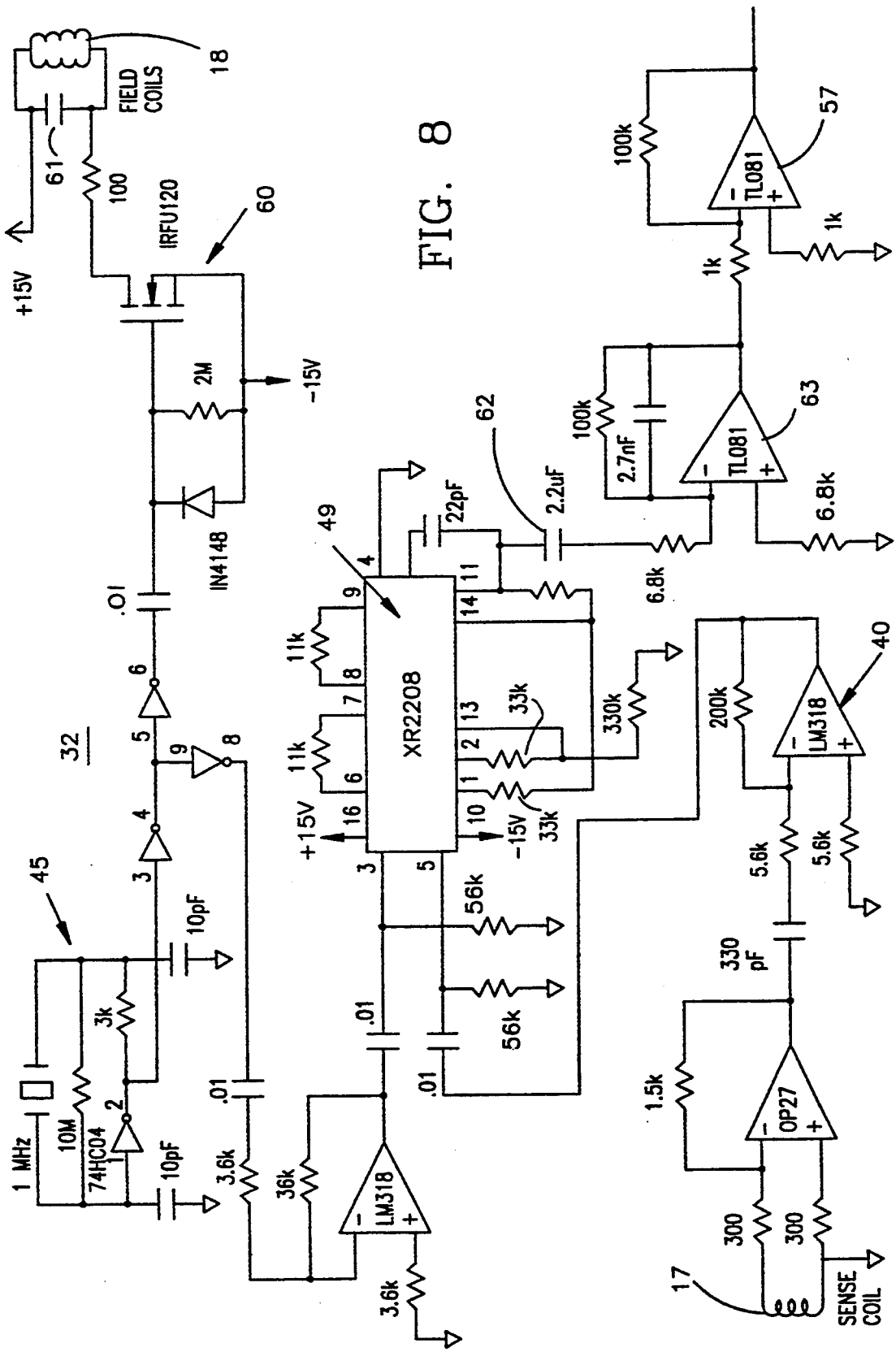
FIG. 8 is a schematic diagram illustrating the components of FIG. 5 in greater detail.

FIG. 8 illustrates the circuit components of the block diagram of FIG. 5. The oscillator 45 comprises a 1 MHz crystal combined in known fashion with resistors, capacitors and inverters. In addition to oscillator 45 the exciter 32 comprises a driver 60 consisting of an FET, resistor and diode as well as a capacitor 61 which is connected across the field coils 18 and forms therewith a resonant circuit. The use of the tuned circuit enhances the field energy provided.

Mixer 49 of FIG. 5 is in the form of an XR2208 multiplier chip having an input pin number 3 connected to oscillator 45 and an input pin number 5 connected to amplifier 40. The mixed output is at pin number 11 and a capacitor 62 serves as the D.C. blocking portion of filter 52 in FIG. 5. The low-pass filter portion of filter 52 is formed of op.amp circuit 63.

It should be noted that the result of the multiplication in the multiplier chip is an output consisting of sum and difference frequencies and harmonics. All of these signal components are in the radio frequency range with the exception of the difference frequency between the 1 MHz reference signal 44 and the sense coil signal 46 (FIG. 6). Since the frequency of these signals is identical, the "difference frequency" output of the multiplier in the absence of a particle target is the D.C. voltage 56 (FIG. 7). When a particle target is present, a characteristic low frequency signature is superimposed on the D.C. voltage 56 as shown in FIG. 7(b). Because all other multiplier outputs are of much higher frequency than particle signatures they can be eliminated by integration in the post-detection amplifier 63 (FIG. 8), leaving only the relevant low-frequency signals. Note that this principle also eliminates almost all interfering R.F. signals and harmonics of the 1 MHz field drive.

Figure 10:
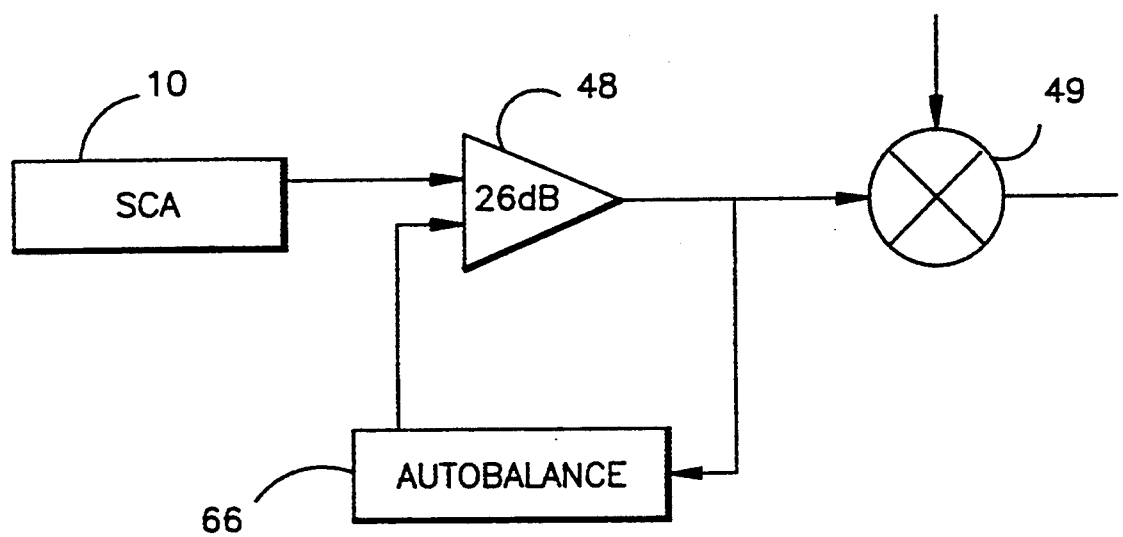
FIG. 10 is a block diagram illustrating an autobalance feature.

The multiplier chip functions on a few mV of signal and so the demand for gain at signal frequency is minimized thus easing design problems with stability. This detector design also reduces balance requirements in the SCA 10 since the main requirement for balance is now dictated by the need to avoid overdriving and saturation of the sense coil signal amplifiers, a condition relatively easy to meet as gain requirements are modest. Although, in principle, the design will operate satisfactorily without any balance provision, if the SCA 10 cannot be manufactured to a sufficiently high tolerance the residual signal 55 may become unacceptably high in which case an automatic balancing (autobalance) circuit may be necessary. FIG. 10 illustrates generally the principle in which an autobalance block 66 is positioned to feed back the output of differential amplifier 40 to an input of differential amplifier 40 in opposition to the signal supplied by SCA 10. The autobalance block 66 feeds back the signal which is obtained when no particle is present to subtract from the signal which is obtained when a particle is present thereby cancelling the residual.

Figure 9:
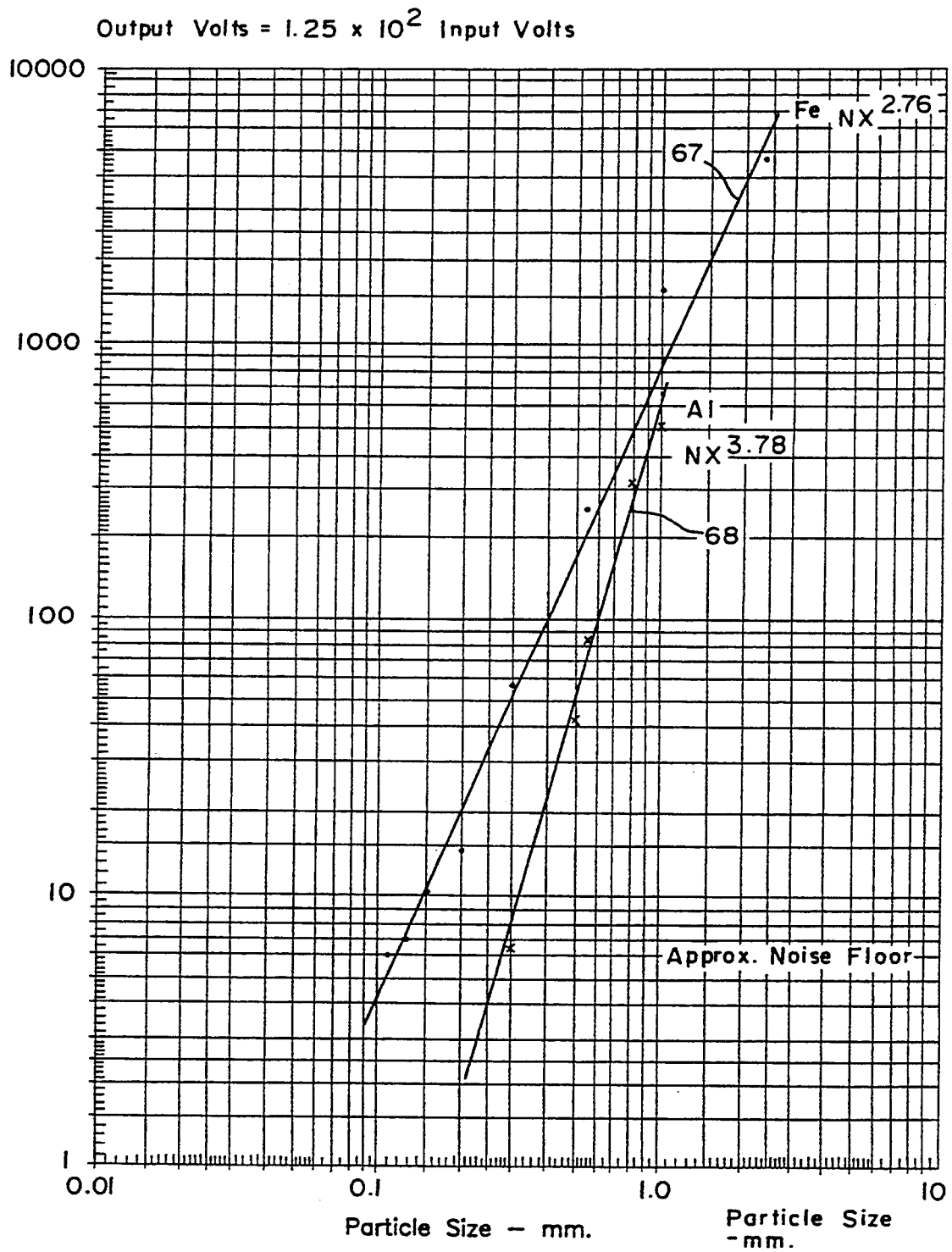
FIG. 9 is a graph illustrating the response of the detector versus particle size for ferrous and aluminum particles.

FIG. 9 shows the relationship found between particle size and amplitude of the sensed signal. Line 67 shows the results for ferrous particles and line 68 for aluminum particles.

Using the present invention spherical ferromagnetic particles of 125 microns or larger in diameter or spherical aluminum particles of about 250 microns or larger in diameter can be detected with high probability.

In addition to the expected ferromagnetic and non-ferromagnetic signature sequences, another phenomenon has been noted. Typically, if the sequence of amplitude and phase changes which constitute a target signature are displayed on a double-beam oscilloscope together with a reference trace derived from the field drive, the normally observed sequence as the target particle traverses the detection region is a growing in-phase signature which reaches a maximum then reverses rapidly to an antiphase condition before fading back to the steady state residual of the sense coil winding (which may display any phase), or the reverse of this sequence, depending on ferromagnetic or non-ferromagnetic nature of the target. A class of targets was found, however, in which a marked excursion in phase of the signature was noted both before and after the central rapid axis-crossing of the signature. This class of targets is identified tentatively as those of a material which is mildly magnetic and also conductive, thus leading to an interaction between non-ferromagnetic and ferromagnetic responses. Perhaps significantly, non-conducting ferrite targets (having only magnetic properties) always display the expected in-phase/antiphase sequence.

Although the present invention is primarily intended for use in discriminating between ferromagnetic and non-ferromagnetic particles and determining the size of the particles, the technique might also yield the measurement of other properties or characteristics. If particles of the same size are detected, copper could be discriminated from aluminum.

In the above description of the invention, the expression "particle size" refers to the character of spherical particles. For non-spherical ferromagnetic particles, the same signature is produced by a particle having the same volume (mass). For non-spherical conductive particles, the same signature is produced by a particle having the same largest conductive loop area.

It should be noted that the sense coil assembly 10 is very sensitive to small mechanical movements of the coils 17 and 18. In the sensor coil assembly 10 shown in FIG. 3 the coils 17 and 18 are formed on a bobbin 16 which is carried on a tubular former 19 through which the oil flows. Small fluctuations in oil pressure due to pump pulsations or turbulence can cause a slight expansion in the diameter of former 19 and the coils 17 and 18. This effectively increases the inductance of the coils which can affect the amplitude and phase of the output signal. These variations produce noise which adversely affects the signature detection.

Figure 11:
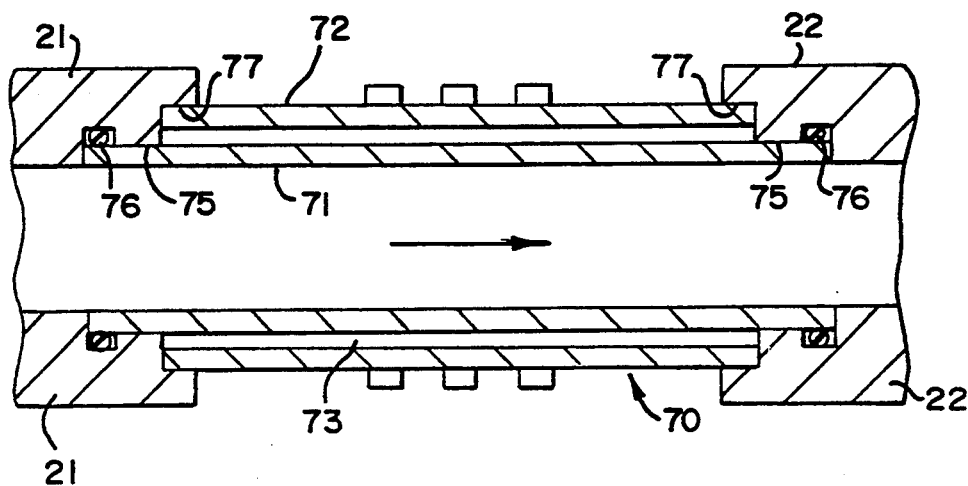
FIG. 11 is a longitudinal sectional view of an improved former for the sensor coil assembly.

In order to eliminate this effect, the former may be redesigned, as shown in FIG. 11, as a double-wall tube 70 comprising an inner tube 71 and a concentric outer tube 72 separated from tube 71 by an air gap 73.

The bobbin 16 carrying coils 17 and 18 is applied to the outer tube 72. The ends of inner tube 71 are received snugly within first recessed portions 75 of pipe sections 21 and 22 and sealed with respect to the pipe sections by means of seals 76. Outer tube 72 is shorter than tube 71 and its ends are received snugly within second recessed portions 77, which have a greater diameter than recessed portions 75, also in pipe sections 21 and 22.

Pressure effects applied to the wall of the inner tube 71 by the oil passing therethrough are not transmitted to the outer tube because the two tubes are not in contact and so the double-walled arrangement of FIG. 11 is less susceptible to noise.

The two tubes may, as with the FIG. 3 embodiment, be made of TORLON but other non-metallic materials could also be used. Typically the air gap 73 is of the order of 0.010 inch.

Figure 11A:
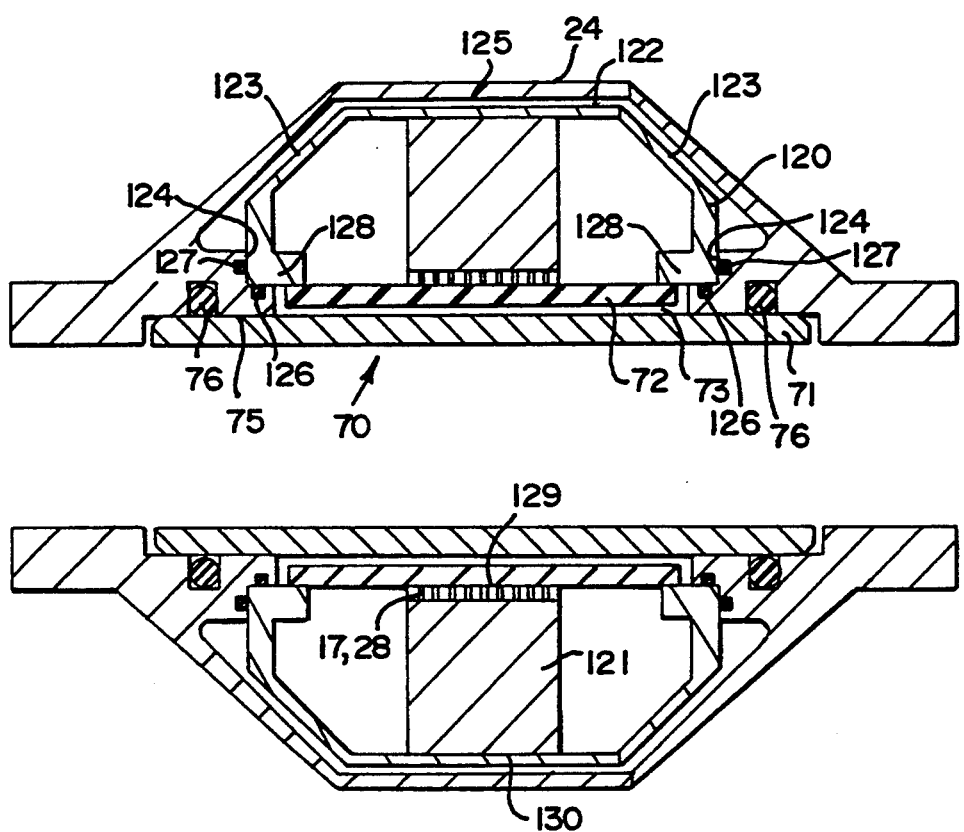
FIG. 11a is a view similar to FIG. 11 but illustrating an improvement intended to isolate the coils from external mechanical vibration.

FIG. 11a illustrates another technique for reducing further movement of the coils 17 and 18. As with the FIG. 11 embodiment the former 70 is designed as a double-wall tube 70 comprising an inner tube 71 and a concentric outer tube 72 separated from tube 71 by an air gap 73.

The ends of the inner tube 71 are, as with the FIG. 11 embodiment, snugly received within recessed portions 75 of pipe sections 21 and 22 and sealed with respect to the pipe sections by means of seals 76. However, outer tube 72 is not connected directly to pipe sections 21 and 22 but is instead supported concentrically with respect to inner tube 71 by means of an inner shield 120 and a coil support sleeve 121 as follows.

The inner shield 120 may be made of a material such as aluminum which provides electromagnetic shielding and has an external profile which is similar to the internal profile of widened portions 25 and 26 of pipe sections 21 and 22 together with sensor body or housing 24. Thus, the inner shield 120 has a central cylindrical portion 122 connected to two sloping end portions 123. The end portions 123 are supported on recessed portions 124 of pipe sections 21 and 22 such that there is an air gap 125 between inner shield 120 and body 24.

To permit assembly, the inner shield is not formed as a unitary member but has a break where the cylindrical portion 122 joins one of the end portions 123. The outer housing or body 24 is similarly formed by two parts for ease of assembly.

The coil support sleeve 121 prevents flexure of either inner shield 120 or outer tube 72 which could occur under vibration loads, from affecting the position of coils 17 and 18.

Circumferential O-rings 126 and axial O-rings 127 are provided in the circumferential and axial walls of the recessed portions 124 and the inner ends 128 of the inner shield are actually supported on those O-rings.

The coil support sleeve 121 has the sense and field coils 17 and 18 provided on a bore 129 which registers with the outer tube 72. The outer cylindrical surface 130 of coil support sleeve 121 engages the cylindrical portion 122 of inner shield 120 in an interference fit. Thus, the coil supporting sleeve 121 positions the coils 17, 18 and outer tube 72 concentrically with respect to inner tube 71. The coil former may be made of a rigid plastics material.

The O-ring supports on which the inner shield 120 rest act like pin joints, i.e., they do not transmit movement from the body 24 to the inner shield 120, support sleeve 121 or coils 17, 18. Thus, any vibration, impact or physical distortion suffered by sensor body 24 is not transmitted to the coils 17, 18.

Figure 12:
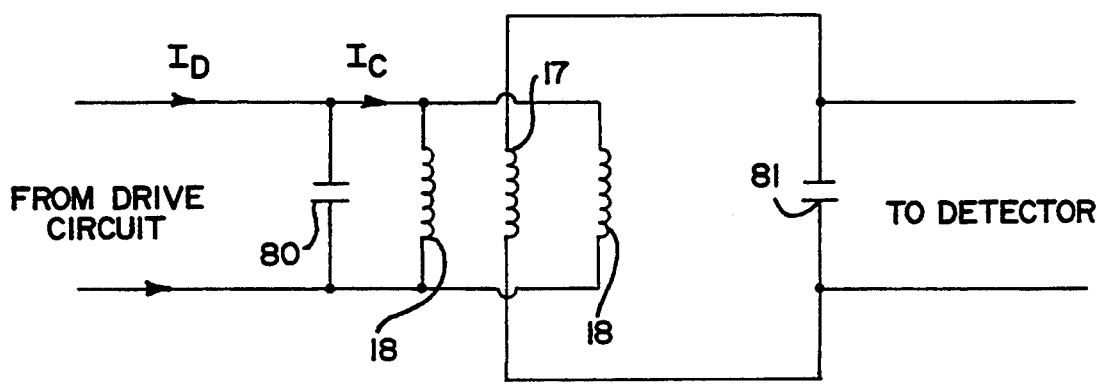
FIG. 12 is a circuit diagram of resonant circuits used to improve the sensitivity of the sensor.

FIG. 12 illustrates a technique for boosting the sensitivity of the sense coil assembly. The field coils 18 are connected in parallel with each other and a capacitor 80 connected in turn across the output from the exciter 32. The field coils and capacitor 80 together form a resonant tank circuit and so when the circuit is driven at resonant frequency current multiplication is achieved. Specifically, current I which circulates through the field coils 18 is related to the drive current $I_D$ by the equation $I_c = Q_1 \cdot I_D$ where $Q_1$ is the quality factor of the resonant c circuit. Typically a $Q_1$ of 25-30 can be obtained.

The same modification can be made to the sense coil 17. That is to say a capacitor 81 is connected across sense coil 17 to form another resonant circuit. The very small magnetic field due to the presence of a particle induces a voltage onto sense coil 17. This voltage $V_p$ is related to the voltage $V_D$ detected on capacitor 81 by the equation $V_D = Q_2 V_p$ where $Q_2$ is the quality factor of the resonant circuit comprising coil 17 and capacitor 81.

Using resonant circuits on both the field and sense coils boosts the sensitivity of the device by $Q_1 \cdot Q_2$ which may be 600 or more.

Figure 13:
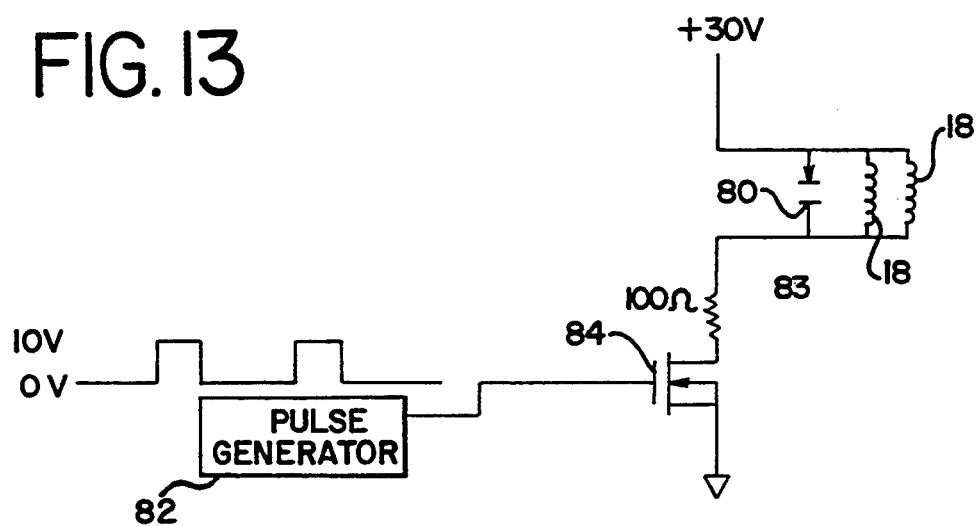
FIG. 13 is a circuit diagram of a pulse drive circuit for increasing the field strength of the field coil.

FIG. 13 illustrates how the magnetic field derived by the field coils 18 may be increased even more. As with the embodiment of FIG. 12 the field coils are connected across capacitor 80 to form a resonant tank circuit. In addition, the resonant circuit is connected through a current limiting resistor 83 to a transistor 84. The resonant circuit, resistor 83 and transistor are together connected across a 30 volt supply and the transistor is gated by 10 volt drive pulses from a pulse generator 82.

The transistor 84 is driven as a Class C amplifier i.e., it is switched on by the drive pulses 85 (FIG. 14a) with less than a 50% duty cycle which is selected to provide minimum power consumption. When the amplifier is off, the resonant circuit forces the voltage 86 (FIG. 14b) to swing to twice the applied voltage which therefore doubles the magnetic field strength.

The drive efficiency can be improved by modifying the pulse waveform as shown in FIG. 14c. Instead of a single pulse applied at regular intervals, three closely spaced pulses are applied, namely a narrow pulse 85' followed by a wider pulse 85Δ followed by a narrow pulse 85'''. This will reduce power consumption and harmonics by ramping the supplied current up and down as the resonant circuit voltage rises and falls.

FIG. 10 illustrates the general principal of autobalance. This will be explained more fully with reference to FIGS. 15 and 16 which illustrate two specific embodiments of autobalance circuit.

As explained with reference to FIGS. 5 and 6, the output of SCA 10 consists of a particle signature signal 46 and an imbalance residual signal 55 which is an undesired signal perhaps three orders of magnitude larger than the signature signal 46. The circuits of FIGS. 15 and 16 both function by generating a replica of the imbalance residual signal which is then subtracted from the output of SCA 10 thereby leaving only the signature signal 46 which can then be detected. The circuits function as control loops, with the voltage at (A) and (J) being the error signals. The control loops are designed to be too slow to respond to the particle signature, so it is not cancelled. Therefore the error signals at (A) and (J) do not contain significant imbalance residual signal, but the signature signal is present. The amplified error voltage at (B) or (K) can be used as the output signal.

Referring now to FIG. 15, the output of SCA 10 is connected to a positive input 90 of a summer 91 which also has a negative input 92 on which a signal I is derived as hereinafter described which is a replica of the imbalance residual signal 55. An error signal A is output from summer 91 and represents the difference signal of the two inputs, i.e., the signature signal 46. The error signal A is passed through an amplifier 93 to obtain an amplified signal B which can then be processed as described with reference to FIGS. 5 and 6 by mixing with a 1 MHz signal, filtering and amplifying to obtain the signal 53 (FIG. 7c).

Reverting to the circuit of FIG. 15, the imbalance residual signal from SCA 10 has an arbitrary phase and amplitude. FIG. 15 contains two amplitude control loops, one controlling the amplitude at a particular phase and the other controlling the amplitude at a phase 90° from the first.

The amplified error signal B is fed to both control loops. The first control loop includes a mixer 94 in which the signal B is multiplied by a 1 MHz carrier signal supplied from generator 45 to produce a signal D which contains two components. The first is a D.C. voltage corresponding to the amplitude of the component of error signal B which is in-phase with the carrier signal and the second is an undesired sum-frequency component. The sum-frequency component is removed by an integrator 95 leaving a control voltage F. The integrator 95 may be replaced with a more complicated circuit to achieve any desired control law. The control voltage F is multiplied in a mixer 96 by the 1 MHz carrier signal to create a replica H of the in-phase component of the amplified error signal B.

A second identical control loop in parallel with the first control loop comprises a mixer 98 followed by an integrator 99 and a mixer 100. However, the 1 MHz carrier is fed through a 90° (quadrature) phase shifter 102 before it is applied to the mixers 98 and 100. Thus, the error signal B is multiplied in mixer 98 by the quadrature carrier signal to produce signal C which contains two components. The first is a D.C. voltage corresponding to the amplitude of the component of B which is in-phase with the quadrature carrier and the second is an undesired sum-frequency component which is filtered out in integrator 99 leaving a control voltage E. Again, the integrator 99 could be replaced with a more complicated circuit to achieve any desired control law. control voltage F is multiplied in the mixer 100 by the quadrature carrier signal to create a replica G of the quadrature component of the amplified error signal B.

The in-phase replica H and the quadrature replica G are summed in a summer 103 to produce the final replica I which, as described above, is subtracted from the signal from SCA 10 to produce error signal A.

Due to the design of the control loops, the replica I does not track rapid variations in the input signal caused by a particle passing through the sensor. As a result, the error signal A contains the particle signature but not the residual signal. The amplified version of the error signal B may be conveniently used as the output signal.

As an alternative arrangement, the control loop can be designed to be fast enough to track the particle signature. The voltages E and F then represent the amplitude of the two phase components of the signature. These can be used as signature outputs.

Figure 16:
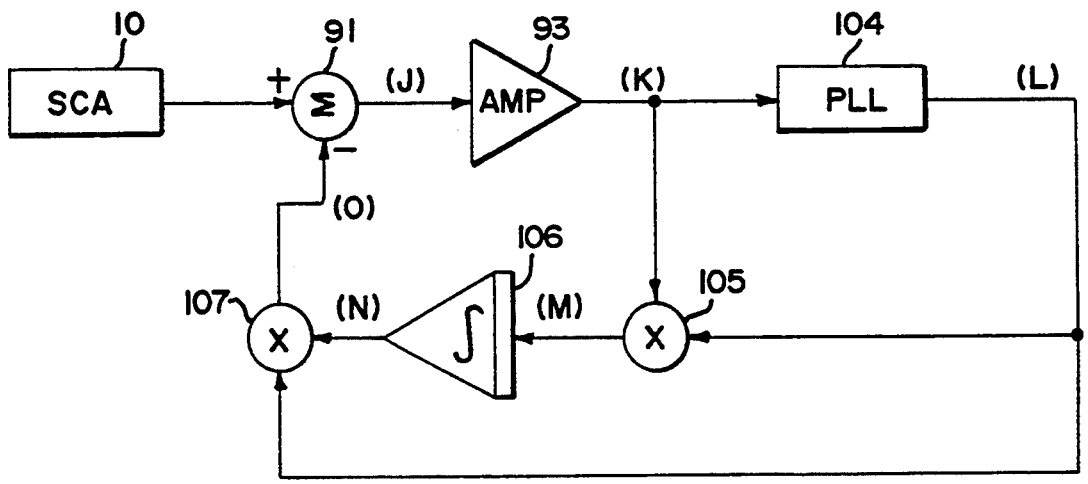
FIG. 16 is a block diagram illustrating an alternative autobalance circuit.

Instead of using two amplitude control loops as in FIG. 15, the amplitude and phase of the imbalance residual may be controlled separately as in the circuit of FIG. 16.

In FIG. 16, the SCA 10 is connected to a summer 91 in turn connected to an amplifier 93 which are identical to summer 91 and amplifier 93 of FIG. 15.

The autobalance circuit is a control loop which attempts to produce a replica O of the imbalance signal from the SCA 10. The signal at O tracks slow variations in the imbalance signal, but does not track the quick changes caused by the passage of a particle through the sensor. The error signal J should therefore contain only the particle signatures. The amplified version of the error signal K can therefore be used as the output signal which must be further processed.

This circuit extracts phase and amplitude information separately from the error signal. The amplified error signal K is fed to a Phase-Locked Loop (PLL) 104 which generates an oscillating signal L which is in phase with the imbalance residual signal. Signal L is then multiplied in a mixer 105 by the error signal K to produce a signal M which contains two components. The first component is a D.C. voltage corresponding to the amplitude of K and the second is an undesired sum-frequency component which is filtered out by an integrator 106 leaving a control voltage N. The integrator circuit could be replaced with a more complicated circuit to achieve any desired control law.

The control voltage N is multiplied in a mixer 107 by the phase-locked signal L to create a replica O of the residual imbalance signal. This is subtracted from the input signal to create the error voltage J, closing the loop. Due to the design of the control loop, the replica 0 does not track rapid variations in the input signal caused by a particle passing through the sensor. As a result, the error signal J contains the particle signature but not the residual signal. The amplified version of the error signal K may be conveniently used as the output signal.

One way of processing signal 53 of FIG. 6d to detect a particle involves the use of a positive threshold detector and a negative threshold detector. A sequence of threshold passages on the two detectors indicates the presence of a particle.

Figure 17:
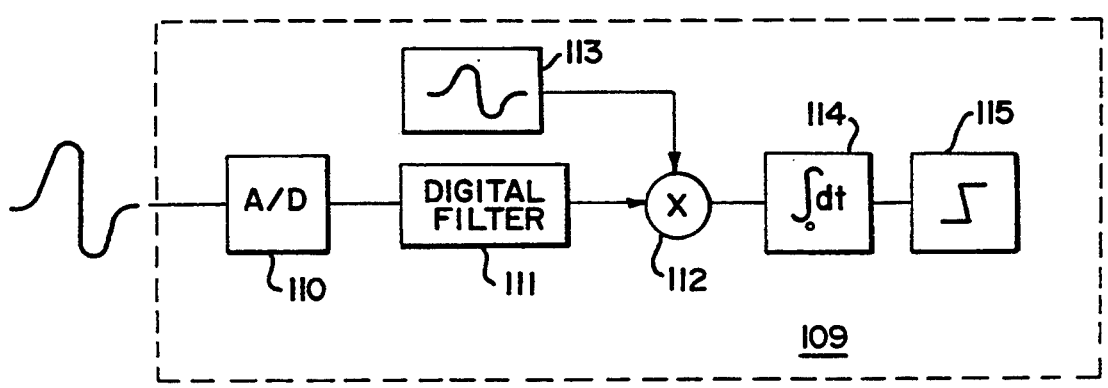
FIG. 17 is a block diagram of a matched filter detector.

An improved detector with better noise rejection uses a matched-filter approach illustrated in FIG. 17.

A matched filter detector compares the signature output of the analog processing electronics to a "model waveform" having the same shape as a typical particle signature. The most practical way to implement this is with a Digital Signal Processor (DSP) 109. First an Analog-Digital Converter 110 changes the signal 53 into a digital representation. A digital filter 111 can be used to eliminate any unwanted noise or interference. The signal is then multiplied in a mixer 112 by the model waveform from waveform generator 113 and integrated by integrator 114 over the duration of the model waveform. This can be repeated for each sample received, in effect sliding a detection window along the data. A large peak occurs on the output of the integrator 114 whenever a signature appears and this is detected by a threshold detector 115. The peak will have different polarities for ferrous and non-ferrous particles. The height of the peak may be used as an indication of the size of the particle. This technique provides improved signal-to-noise performance over the simple threshold detector approach. Also, the DSP 109 can monitor noise conditions and dynamically adjust the threshold to avoid false counting.

In order to account for variations in flow speed several model waveforms of different durations can be matched simultaneously with the same signature signal. They can either be run in parallel or selected based upon an input from a flow rate sensor, pump speed sensor or similar device.

We claim:

1. Apparatus for detecting the presence of solid ferromagnetic particles or solid non-ferromagnetic conductive particles entrained in a stream of fluid comprising at least one sense and at least one field coil supported coaxially on a tubular non-metallic former through which the stream of fluid passes, the former having an inner tubular wall and an outer tubular wall separated from the inner tubular wall by an air gap whereby fluctuations in the pressure of the stream of fluid do not cause movement of the outer tubular wall, means for energizing the field coil to generate an A.C. magnetic field and establish an A.C. magnetic field at the sense coil, means connected to the sense coil to detect a disturbance of the A.C. magnetic field present at the sense coil when a particle moves through the coils, and a protective housing enclosing the former and coils and means isolating the outer tube from movement of the housing, wherein the isolating means comprises an inner shield located inside the housing, spaced therefrom and enclosing the outer tube and coils, the inner shield being supported on the housing at pin joints which do not transmit movement from the housing to the inner shield, the coils being carried at a bore of a coil support sleeve the bore of which registers with and engages the outer tube and an outer circumferential surface of which engages the inner shield.

2. Apparatus according to claim 1 in which the pin joints are provided by circumferential and axial O-rings.

3. Apparatus for detecting the presence of solid ferromagnetic particles or solid non-ferromagnetic conductive particles entrained in a stream of fluid comprising three coaxial coils arranged to encompass the stream, one of the coils being a sense coil and the other coils being field coils located respectively upstream and downstream with reference to the sense coil, one field coil being wound in a first direction and the other field coil being wound in the opposite direction, means for energizing the field coils to generate A.C. magnetic fields and establish opposing A.C. magnetic fields at the sense coil, means connected to the sense coil to detect a disturbance of the A.C. magnetic field present at the sense coil when a particle moves through the coils and to provide a signature electrical signal indicative of a disturbance, means for removing any residual electrical signal due to imbalance of the opposing A.C. magnetic fields from that signature electrical signal and provide an output signal and means to analyze the phase of the output signal so as to discriminate between ferromagnetic and non-ferromagnetic conductive particles, wherein the sense and field coils are supported on a tubular non-metallic former through which the stream of fluid passes, the former having an inner tubular wall and an outer tubular wall separated from the inner tubular wall by an air gap whereby fluctuations in the pressure of the stream of fluid do not cause movement of the outer tubular wall.

4. Apparatus according to claim 3 further comprising a protective housing enclosing the former and coils and means isolating the outer tube from movement of the housing.

5. Apparatus according to claim 4 wherein the isolating means comprises an inner shield located inside the housing, spaced therefrom and enclosing the outer tube and coils, the inner shield being supported on the housing at pin joints which do not transmit movement from the housing to the inner shield, the coils being carried at a bore of a coil support sleeve the bore of which registers with and engages the outer tube and an outer circumferential surface of which engages the inner shield.

6. Apparatus according to claim 3 in which the sense coil is connected to a capacitor to form a resonant tank circuit to obtain voltage magnification in the sense coil.

7. Apparatus according to claim 3 in which the means for energizing the field coils is a pulse drive.

8. Apparatus according to claim 7 in which the pulse drive provides successive groups of three pulses comprising a relatively narrow pulse followed by a relatively wide pulse in turn followed by a relatively narrow pulse whereby the drive current is ramped up and down.

9. Apparatus according to claim 3 in which the means for removing any residual electrical signal is an autobalance circuit having two feedback loops and comprising a summing circuit having a positive input connected to an output from the sense coil and a negative input connected to an output of the two feed back loops and having an output connected to an input of the two feedback loops, one of the two feedback loops deriving a replica of the in-phase component of the error signal and the other feedback loop deriving a replica of the quadrature component of the error signal.

10. Apparatus according to claim 3 in which the means for removing any residual electrical signal is an autobalance circuit having a feedback loop and comprising a summing circuit having a positive input connected to an output from the sense coil and a negative input connected to an output of the feedback loop and having an output connected to an input of the feedback loop, the feedback loop including a phase-locked loop and deriving an in-phase replica of the error signal.

11. Apparatus according to claim 3 further comprising processing circuitry for processing the output signal to detect a particle, the processing circuits comprising means generating a model waveform having the same shape as a typical particle and means for comparing the output signal with the model waveform and detect when a match is made.

12. Apparatus according to claim 5 in which the processing circuitry comprises an analog detector having an input for the output signal, a digital filter fed by the analog detector and feeding to one input of a mixer another input of which is fed by the model waveform generating means, an integrator fed by an output of the mixer and a threshold detector fed by the integrator.

* * * * *